United States Patent [19]
Shibayama et al.

[11] Patent Number: 6,121,196
[45] Date of Patent: Sep. 19, 2000

[54] AGENT FOR PREVENTING GROWTH OF WEEDS IN RICE FIELDS

[75] Inventors: Hidejiro Shibayama, Karatsu; Tadamitsu Nakamura, Yoshikawa; Takuji Kihara; Shinichi Ogawa, both of Tokyo; Fujiko Yamashita, Kitakatsushika-gun, all of Japan

[73] Assignee: Dainichiseika Color & Chemicals Mfg. Co., Ltd., Tokyo, Japan

[21] Appl. No.: 09/205,748

[22] Filed: Dec. 4, 1998

[51] Int. Cl.$^7$ .............................. A01N 43/16; A01N 59/00
[52] U.S. Cl. .............................................. 504/150; 504/151
[58] Field of Search ...................................... 504/150, 151

[56] References Cited

U.S. PATENT DOCUMENTS 4,482,467  11/1984  Nakamura et al. ....................... 252/70

FOREIGN PATENT DOCUMENTS 7-313002  12/1995  Japan .

*Primary Examiner*—S. Mark Clardy
*Attorney, Agent, or Firm*—Frishuaf, Holtz, Goodman, Langer & Chick, P.C.

[57] ABSTRACT

A herbicidal composition for preventing the growth of weeds in rice fields which comprises active carbon in a powder form dispersed in water in the presence of a starch or a derivative of starch. The herbicidal composition prevents the growth of weeds on the surface of soil covered with water in a rice field by decreasing the amount of light which passes through the water covering the soil. The herbicidal composition does not cause any problem regarding food sanitation, maintains the effect for a long period of time with stability by repeated applications, is inexpensive and can be used advantageously.

17 Claims, No Drawings

AGENT FOR PREVENTING GROWTH OF WEEDS IN RICE FIELDS

BACKGROUND OF THE INVENTION

1. Field of the Invention

The present invention relates to an agent for preventing growth of weeds in rice fields. More particularly, the present invention relates to an agent for preventing growth of weeds in rice fields which is added to water in rice fields to prevent growth of weeds on the surface of soil covered with water in the rice fields by decreasing the amount of light which passes through water covering the soil, does not cause any problem of food sanitation, maintains the effect for a long period of time with stability by repeated applications, is inexpensive and can be used advantageously.

2. Description of the Related Arts

Prevention of growth of weeds in rice fields means control of growth of weeds which compete with rice and maintenance of advantageous conditions in rice fields. Growing rice has been a battle against weeds since ancient times. Huge amounts of labor have been used to remove weeds from rice fields while rice fields used by the human kind have continued to expand. Recently, herbicides which can maintain growth of plants of the rice family and selectively remove weeds in rice fields have been developed and widely used. Although these herbicides satisfy the requirements that they be decomposed in the natural environment, not be accumulated in animals and plants and show no chronic toxicity to human bodies, application of some herbicides is voluntarily discontinued.

Due to the tendency of consumers to prefer natural products and to emphasize sanitation, rice is increasingly required to be grown without using agricultural chemicals. Thus, development of methods of removing weeds in rice fields without using herbicides has been attempted. For example, growth of weeds can be prevented by raising ducks, Triopus longicaudatus or carps in rice fields. Suppressing growth of weeds by intentionally growing algae has been also attempted. It is also attempted that a China ink is added to rice fields to suppress the growth of weeds by the effect of shielding the rice field from light and rice is grown without using agricultural chemicals. However, raising animals has a drawback in that it requires a large amount of labor for the management. Growing algae has drawbacks in that it occasionally causes adverse effects on rice and that algae do not always dominate weeds in the competition. Carbon black which is the raw material of China inks is not free from problems of food sanitation because it is produced from petroleum, natural gas or acetylene although it is kept under the regulation on the food sanitation which requires that benzopyrene be not detected.

Therefore, an agent for preventing growth of weeds in rice fields which causes no problem at all with respect to the food sanitation, exhibits excellent effect of preventing growth of weeds in rice fields, is inexpensive and can be used economically has been desired.

SUMMARY OF THE INVENTION

The present invention has an object to provide an agent for preventing growth of weeds in rice fields which is added to water in rice fields to prevent growth of weeds on the surface of soil covered with water in the rice fields by decreasing the amount of light which passes through water covering the soil, does not cause any problem of food sanitation, maintains the effect for a long period of time with stability by repeated applications, is inexpensive and can be used advantageously.

As the result of extensive studies by the present inventors to solve the above problems, it was found that a dispersion prepared by finely dispersing active carbon in a powder form in water in the presence of a dispersant exhibits an excellent effect to prevent growth of weeds in rice fields. The present invention has been completed on the basis of this knowledge.

Accordingly, the present invention provides:

(1) An agent for preventing growth of weeds in rice fields which comprises active carbon in a powder form dispersed in water in the presence of a dispersant;

(2) An agent described in (1), wherein particles of the active carbon in a powder form dispersed in water have an average diameter of 20 µm or less;

(3) An agent described in any of (1) and (2), wherein the content of the active carbon in the agent is 1 to 40% by weight based on the total weight of the agent;

(4) An agent described in any of (1), (2) and (3), wherein the dispersant is one or more substances selected from the group consisting of soybean polysaccharides soluble in water, starch, derivatives of starch, caramel, sodium alginate, sodium carboxymethylcellulose and polyvinylpyrrolidone; and (5) An agent described in any of (1), (2), (3) and (4), wherein the content of the dispersant in the agent is 1 to 40% by weight based on the total weight of the agent.

DESCRIPTION OF THE PREFERRED EMBODIMENTS

In the agent for preventing growth of weeds in rice fields of the present invention, active carbon in a powder form is used as the material for decreasing the amount of light which passes through water covering the soil. The average diameter of particles of the used active carbon in a powder form is preferably 20 µm or less, more preferably 10 µm or less and most preferably 5 µm or less. When the average diameter of particles of the active carbon exceeds 20 µm, dispersion of the active carbon becomes inferior and the effect to prevent growth of weeds in rice fields decreases. Moreover, there is the possibility that the storage stability of the agent deteriorates because of precipitation of the particles of the active carbon.

The active carbon in a powder form is dispersed with stability in water covering rice fields for a long period of time and effectively prevents growth of weeds from the soil covered with water by decreasing the amount of light which passes through the water. The agent for preventing growth of weeds in rice fields of the present invention has a low viscosity and exhibits an excellent fluidity because particles of the active carbon in a powder form have an average diameter of 20 µm or less and are finely dispersed in water. Therefore, the agent diffuses uniformly throughout the entire area of a rice field when the agent is quietly added dropwise to water at an inlet of the water to the rice field. The agent may also be spread in the entire area of a rice field using a bottle or a sprinkling can.

The active carbon in a powder form used in the present invention is not particularly limited and active carbon obtained from sawdust, coconut husk or coal and activated with a chemical or water vapor can be used. Commercial active carbon in a powder form can be used and commercial active carbon in a granular form can also be used after pulverization. Active carbon has been used for a long period of time in the area related to drinks and foods. For example, active carbon has been used for water treatment in water supply, purification of beer, wine and soy sauce in the brewing industry, purification of drugs and the whitening of purified sugar. Therefore, the safety of active carbon in application to foods has been established for a long time. Active carbon does not easily flow out of rice fields because the true density of active carbon is about 2 g/cm$^3$. Active carbon has numerous fine pores to give a large surface area and adsorbs various types of molecules to the surface. Therefore, active carbon holds fertilizers and agricultural chemicals in water in rice fields by adsorption and the effect exhibited by active carbon can be maintained for a long period of time. Carbon black has an advantage in that it can also be dispersed easily. However, when carbon black is added to water in a rice field, there is the possibility that carbon black remains floating on the surface of water and is lost by flowing out of the rice field into rivers. Moreover, carbon black is not free from the problems of food sanitation because carbon black has not been approved as a food additive.

It is preferable that the agent for preventing growth of weeds in rice fields of the present invention contains the active carbon in a powder form in an amount of 1 to 40% by weight and more preferably 5 to 30% by weight based on the total weight of the agent. When the content of the active carbon in a powder form is less than 1% by weight, an excessively large amount of the agent for preventing growth of weeds in rice fields must be added to water in the rice field and the content is not practically advantageous. When the content of the active carbon exceeds 40% by weight, the stability of the dispersion tends to decrease.

The dispersant used for the agent for preventing growth of weeds in rice fields of the present invention is not particularly limited as long as the dispersant show an excellent effect of dispersing the active carbon in a powder form and causes no problem with respect to food sanitation. Examples of the dispersant include soybean polysaccharides soluble in water, starch, derivatives of starch, caramel, sodium alginate, sodium carboxymethylcellulose and polyvinylpyrrolidone. The dispersant can be used singly or as a combination of two or more types.

The soybean polysaccharides soluble in water which are used as the dispersant are not particularly limited. For example, soybean polysaccharides soluble in water which are obtained by extracting refuse formed in the preparation of soybean protein as a byproduct by heating in a weakly acidic condition after adding water can be used as the dispersant. The soybean polysaccharides soluble in water contain galactose, arabinose and galacturonic acid as the main components and many other components such as rhamnose, fucose, xylose and glucose. The soybean polysaccharides soluble in water are considered to have a structure in which galactan and arabinan are bonded to the main chain formed with galacturonic acid. The soybean polysaccharides soluble in water generally have an average molecular weight of several hundred thousands. Polysaccharide soluble in water generally show a lower viscosity than that of conventional polysaccharide thickeners such as guar gum and an aqueous dispersion having a concentration as high as 30% by weight or more can be prepared. An aqueous dispersion of soybean polysaccharides exhibits excellent heat resistance and acid resistance and the viscosity of the aqueous dispersion is hardly affected by the presence of salts. The soybean polysaccharides soluble in water are considered to be adsorbed to the active carbon in a powder form through anions of the galacturonic acid in the main chain to form a layer of the polysaccharides around the active carbon and prevents aggregation of particles of the active carbon by repulsive force between the formed charge.

The soybean polysaccharides soluble in water are food fibers derived from soybeans and are approved as a food additive in accordance with the Food Sanitation Act. Therefore, the polysaccharides are used in foods such as milk drinks, cold cookies, baked cookies, meringues and dried noodles and cause no problem with respect to the food sanitation. As the soybean polysaccharides soluble in water, commercial products may be used. Examples of the commercial product include SOYAFIVE-S series products such as SOYAFIVE S-DN, SOYAFIVE EN100, SOYAFIVE S-LA200 and SOYAFIVE S-FA100 (all trade names; manufactured by FUJI SEIYU Co., Ltd.).

The starch used as the dispersant is not particularly limited. Examples of the starch include starch separated from corn, potato, sweet potato, cassaba, wheat and rice. Starch has been used for a long period of time directly as a food material and as a material for cookies such as biscuits, thick malt syrup and glucose. Starch is consumed in a large amount and causes no problem with respect to food sanitation.

The derivative of starch used as the dispersant is not particularly limited. Examples of the derivative of starch include soluble starch, dextrin, British gum and oxidized starch. These derivatives of starch have been widely used as a shaping material for drugs and an additive for foods and cause no problem with respect to food sanitation.

The caramel used as the dispersant is a black brown material obtained by heating a sugar such as glucose and sucrose. The caramel is easily soluble in water and has been used as a coloring agent for soy sauce, sauce, foods such as cookies and cakes and drinks such as whisky. Therefore, the caramel causes no problem with respect to food sanitation.

Sodium alginate used as the dispersant can be obtained from calcium alginate contained in brown algae by converting calcium alginate to the sodium salt with an aqueous solution of sodium carbonate and extracting the sodium salt. Sodium alginate is used in a large amount as a stabilizer for ice cream and has been approved as a food additive. Therefore, sodium alginate causes no problem with respect to the food sanitation.

Sodium carboxymethylcellulose used as the dispersant can be obtained by the reaction of sodium chloroacetic acid with alkali cellulose which is obtained by the reaction of an alkali with cellulose. Sodium carboxymethylcellulose is used as a stabilizer for ice cream and jam and has been approved as a food additive. Therefore, sodium carboxymethyl-cellulose causes no problem with respect to food sanitation.

Polyvinylpyrrolidone used as the dispersant is a polymer of N-vinyl-2-pyrrolidone and is easily available as a commercial product such as KOLLIDON 30 (trade name, manufactured by BASF Company). Polyvinylpyrrolidone has been approved by FDA as a material for cosmetics and a clarifying agent in brewing beer and causes no problem with respect to food sanitation.

In the agent for the preventing the growth of weeds in rice fields of the present invention, the content of the dispersant is preferably 1 to 40% by weight and more preferably 5 to 30% by weight based on the total weight of the agent. When the content of the dispersant is less than 1% by weight, the effect of dispersing the active carbon in a powder form is insufficient and there is the possibility that the active carbon in a powder form aggregates or precipitates. When the content of the dispersant exceeds 40% by weight, the effect of improving dispersion is not exhibited to the degree expected from the content and there is the possibility that the agent becomes economically disadvantageous.

The agent for preventing the growth of weeds in rice fields of the present invention can be prepared by uniformly dispersing the active carbon in a powder form into water in the presence of the dispersant. The process for dispersing the active carbon in a powder form is not particularly limited. For example, the dispersion can be conducted using a dispersing machine such as a sand mill and a speed line mill. In the process for dispersing the active carbon in a powder form, it is preferable that the active carbon is sufficiently dispersed so that the average diameter of the active carbon is 20 μm or less, preferably 10 μm or less and most preferably 5 μm or less.

It is preferable that the agent for preventing the growth of weeds in rice fields of the present invention is added to water in a rice field in such an amount that the concentration of the active carbon in the water is 5 to 200 ppm and more preferably 20 to 100 ppm. When the concentration of the active carbon in water in the rice field is less than 5 ppm, there is the possibility that the effect of the agent to prevent the growth of weeds is not sufficiently exhibited when the rice field has a depth of water of 5 cm or less. The concentration of the active carbon of 200 ppm in water is sufficient for preventing growth of weeds in a rice field and it is generally not necessary that the active carbon is contained in a concentration exceeding 200 ppm.

By adding the agent for preventing the growth of weeds in rice fields of the present invention to water in a rice field, the growth of weeds in water covering the soil of the rice field can be prevented and, when there is any growth of weeds, the growth can be suppressed. Therefore, plants of the rice family can be raised without using herbicides with little labor in the absence of the effect of weeds.

To summarize the advantages of the present invention, the agent for preventing the growth of weeds in rice fields of the present invention causes no problem with respect to food sanitation when it is added to water of a rice field, effectively prevents the growth of weeds on the soil covered with water and maintains the advantageous effect with stability for a long period of time by repeated additions to the water.

EXAMPLES

The present invention is described more specifically with reference to the following examples. However, the present invention is not limited to the examples.

In Examples 1, 3, 9 and the comparative Example 1, weeds which grew spontaneously from the test soil were Monochoria vaginalis var. plantaginea Solms-Laub., Cyperacae, Rotala indica Koehne var. Uliginosa Miq., Lindernia pyxidaria L. and Elatine orientalis Makino. Plants of the Echinochloa crus-galli Beau family were found scarcely and not counted as the weeds.

Preparation Example 1 (Herbicidal Composition A for preventing the growth of weeds in rice fields)

Active carbon in a powder form (manufactured by FUTA-MURA KAGAKU KOGYO Co., Ltd.; trade name, TAIKO S) in an amount of 10 parts by weight, 10 parts by weight of soluble starch (manufactured by NICHIDEN KAGAKU Co., Ltd.; trade name, OSK-03α) and 80 parts by weight of water were mixed together and the prepared mixture was treated for dispersion by a sand mill until the average particle diameter became 5 μm or less to obtain herbicidal composition A for preventing the growth of weeds in rice fields.

Preparation Example 2 (Herbicidal Composition B for preventing growth of weeds in rice fields)

Active carbon in a powder form (manufactured by FUTA-MURA KAGAKU KOGYO Co., Ltd.; trade name, TAIKO K) in an amount of 10 parts by weight, 10 parts by weight of polyvinylpyrrolidone (manufactured by BASF Company; trade name, KOLLIDON 30) and 80 parts by weight of water were mixed together and the prepared mixture was treated for dispersion by a sand mill until the average particle diameter became 5 μm or less to obtain herbicidal composition the B for preventing the growth of weeds in rice fields.

Example 1

(Effect of preventing the growth of weeds in rice fields)

On Jul. 18, 1994, pots of 1/2000 a were filled with soil for a rice field. The pots were prepared for transplantation after application of an NPK chemical fertilizer (14-16-14) in such an amount that the amount of the N component was 1 kg/a and two rice plants were planted in each pot. On July 19, a dilute dispersion of herbicidal composition A for preventing the growth of weeds in rice fields was added to each pot to prepare pots adjusted to the following conditions: the concentration of the active carbon, 2.5 ppm and the depth of water covering the soil, 3 cm; the concentration of the active carbon, 5 ppm and the depth of water covering the soil, 3 cm; the concentration of the active carbon, 5 ppm and the depth of water covering the soil, 5 cm; and the concentration of the active carbon, 10 ppm and the depth of water covering the soil, 3 cm. The dilute dispersion of the agent for preventing the growth of weeds in rice fields was added to the pots by directly pouring the dispersion from a container to the surface of the soil in the vicinity of the wall of the pot. When the dispersion was added, the flow of the added dispersion gave rise to upward movement of the soil at the surface of the prepared field and a dispersion was formed with the poured black dispersion and the soil. A pot which had the depth of water covering the soil of 3 cm and contained no agent was also prepared in accordance with the same procedure except that the agent was not added. The test was conducted in four pots in each condition.

On August 5, the number of weeds per one pot was counted. Then, the weeds were dried and the weight of the dried weeds was measured. When no agent for preventing the growth of weeds in rice fields was added, 474 weeds were found per one pot in average and the weight of the dried weeds was 3.0 g per one pot. When the concentration of the active carbon was 2.5 ppm and the depth of water covering the soil was 3 cm, 578 weeds were found per one pot in average and the weight of the dried weeds was 3.0 g per one pot. When the concentration of the active carbon was 5 ppm and the depth of water covering the soil was 3 cm, 340 weeds were found per one pot in average and the weight of the dried weeds was 1.7 g per one pot. When the concentration of the active carbon was 5 ppm and the depth of water covering the soil was 5 cm, 334 weeds were found per one pot in average and the weight of the dried weeds was 1.8 g per one pot. When the concentration of the active carbon was 10 ppm and the depth of water covering the soil was 3 cm, 330 weeds were found per one pot in average and the weight of the dried weeds was 2.0 g per one pot.

The results are shown in Table 1.

TABLE 1

| concentration of active carbon (ppm) | depth of water (cm) | number of weeds (/pot) | dried weight of weeds (g/pot) |
|---|---|---|---|
| 0 | 3 | 474 | 3.0 |
| 2.5 | 3 | 578 | 3.0 |
| 5 | 3 | 340 | 1.7 |
| 5 | 5 | 334 | 1.8 |
| 10 | 3 | 330 | 2.0 |

The results in Table 1 show that, while the effect of preventing the growth of weeds in the rice field could not be found when the concentration of the active carbon was 2.5 ppm, the effect could be found when the concentration of the active carbon was 5 to 10 ppm. However, the effect was not satisfactory even when the depth of water covering the soil was 5 cm or the concentration of the active carbon was 10 ppm.

Example 2
(Method of addition of an agent for preventing the growth of weeds in rice fields)

On Oct. 19, 1995, pots of 1/5000 a were filled with soil for a rice field, fertilized and prepared for transplantation in accordance with the same procedures as those conducted in Example 1. After one day, a dilute dispersion of herbicidal composition B for preventing the growth of weeds in rice fields having a concentration of the active carbon of 10 ppm was sprayed from a spray can. After two days, the same dispersion was poured into the rice fields from an Erlenmeyer flask. After five days, the same dispersion was added either by spraying from a spray can or by pouring from an Erlenmeyer flask. The depth of water covering the soil was 3 cm. The test was conducted in two pots in each condition.

The condition of blackness of the water covering the soil was visually observed for one week. The blackness was maintained for a longer time when the dispersion was sprayed from a spray can.

Example 3
(Effect of preventing the growth of weeds in rice fields)

On May 17, 1995, 28 pots of 1/5000 a were filled with soil for rice fields in accordance with the same procedures as those conducted in Example 1. The pots were fertilized and prepared for transplantation on May 19. On May 22, dilute dispersions of herbicidal composition A for preventing the growth of weeds in rice fields having the concentrations of the active carbon of 5 ppm and 10 ppm were applied to four pots for each dispersion using a spray can so that the depth of water covering the soil was 3 cm. On May 25, dilute dispersions of herbicidal composition A for preventing the growth of weeds in rice fields having the concentrations of the active carbon of 10 ppm and 20 ppm were applied to four other pots for each dispersion using a spray can so that the depth of water covering the soil was 3 cm. On May 28, dilute dispersions of herbicidal composition A for preventing the growth of weeds in rice fields having the concentrations of the active carbon of 20 ppm and 40 ppm were applied to four still other pots using a spray can so that the depth of water covering the soil was 3 cm. Four pots were kept without adding the agent. Thus, all tests were conducted in four runs in each condition.

On June 10, grown weeds were taken out and the raw weight of the weeds per one pot was measured. When the agent for preventing the growth of weeds in rice fields was not added, the raw weight of the weeds was 5.0 g. The weight of the weeds in the pots to which the herbicidal composition was added was as follows: 2.7 g in the pots to which the dilute dispersion having the concentration of the active carbon of 5 ppm was added on May 22; 3.5 g in the pots to which the dilute dispersion having a concentration of the active carbon of 10 ppm was added on May 22; 2.9 g in the pots to which the dilute dispersion having concentration of the active carbon of 10 ppm was added on May 25; 2.4 g in the pots to which the dilute dispersion having concentration of the active carbon of 20 ppm was added on May 25; 1.7 g in the pots to which the dilute dispersion having concentration of the active carbon of 20 ppm was added on May 28; and 1.2 g in the pots to which the dilute dispersion having concentration of the active carbon of 40 ppm was added on May 28.

The obtained results are shown in Table 2.

TABLE 2

| date of application of agent | concentration of active carbon (ppm) | weight of raw weeds (g/pot) |
|---|---|---|
| — | 0 | 5.0 |
| May 22 | 5 | 2.7 |
| May 22 | 10 | 3.5 |
| May 25 | 10 | 2.9 |
| May 25 | 20 | 2.4 |
| May 28 | 20 | 1.7 |
| May 28 | 40 | 1.2 |

As shown in Table 2, when the dispersion of herbicidal composition A for preventing the growth of weeds in rice fields having a concentration of the active carbon of 40 ppm was added, a remarkable effect of the herbicidal composition to suppress the growth of the weeds was exhibited with respect to the raw weight of the weeds although the number of the weeds on the day of counting was not much different from the number of the weeds in the pots to which no herbicidal composition was added because of weeds grown in a later period of the test.

Comparative Example 1
(Effect of preventing the growth of weeds in rice fields)

On Jul. 22, 1995, 9 pots of 1/2000 a were filled with soil for rice fields, fertilized and prepared for transplantation in accordance with the same procedures as those conducted in Example 3. Then, two rice plants were planted in each pot. On July 26, a dilute dispersion of herbicidal composition B for preventing the growth of weeds in rice fields having a concentration of the active carbon of 40 ppm was applied to 6 pots using a spray can so that the depth of water covering the soil was 3 cm. On August 3, a dilute dispersion containing herbicidal composition B in the same amount as that used above was applied to 3 pots selected from the 6 pots which had been applied with herbicidal composition B in the above using a spray can so that the depth of water covering the soil was 3 cm (the second addition). All tests were conducted in three runs in each condition including the pots in which no herbicidal composition was added.

On August 21, weeds in the pots to which the herbicidal composition was not added, in the pots to which the herbicidal composition was added once and in the pots to which the herbicidal composition was added twice were examined and the number and the dried weight of the weeds per one pot were obtained. In the pots to which no herbicidal composition was added, the number of the weeds was 372 and the dried weight of the weeds was 13.0 g. The number of the weeds and the dried weight of the weeds were 66 and 3.6 g, respectively, in the pots to which the agent was added once and 19 and 1.4 g, respectively, in the pots to which the herbicidal composition was added twice.

The obtained results are shown in Table 3.

TABLE 3

|  | number of weeds (/pot) | weight of dried weeds (g/pot) |
|---|---|---|
| no application of agent | 372 | 13.0 |
| agent applied once | 66 | 3.6 |
| agent applied twice | 19 | 1.4 |

Although the above test was conduced in the period of the end of July to August when the number of growth of weeds generally decreases, the effect of the herbicidal composition of the present invention is clearly shown in Table 3. When the dilute dispersion of the herbicidal composition of the present invention having a concentration of the active carbon of 40 ppm was applied once, the growth of the weeds decreased to about one quarter of that in the pots to which no herbicidal composition was added. When the above agent was applied twice, the growth of the weeds decreased to one tenth or less of that in the pots to which no agent was added.

Example 4
(Preparation of an agent for preventing the growth of weeds in rice fields)

Active carbon in a powder form (manufactured by FUTAMURA KAGAKU KOGYO Co., Ltd.; trade name, TAIKO S) in an amount of 10 parts by weight, 10 parts by weight of soybean polysaccharides soluble in water (manufactured by FUJI SEIYU Co., Ltd.; trade name, SOYAFIVE S-DN) and 80 parts by weight of water were mixed together and the prepared mixture was treated for dispersion by a sand mill until the average particle diameter became 5 μm or less to obtain agent C for preventing the growth of weeds in rice fields.

Example 5
(Preparation of an agent for preventing the growth of weeds in rice fields)

Tapioca starch in an amount of 10 parts by weight and 80 parts by weigh of water were mixed together and the mixture was heated at 70° C. for 1 hour to dissolve tapioca starch into water. After the prepared solution was cooled to room temperature, 10 parts by weight of active carbon in a powder form (manufactured by FUTAMURA KAGAKU KOGYO Co., Ltd.; trade name, TAIKO S) was added to the solution and the prepared mixture was treated for dispersion by a sand mill until the average particle diameter became 5 μm or less to obtain agent D for preventing the growth of weeds in rice fields.

Example 6
(Preparation of an agent for preventing the growth of weeds in rice fields)

Agent E for preventing the growth of weeds in rice fields was prepared in accordance with the same procedures as those conducted in Example 7 except that 10 parts by weight of caramel was used in place of 10 parts by weight of soybean polysaccharides soluble in water.

Example 7
(Preparation of an agent for preventing the growth of weeds in rice fields)

Agent F for preventing the growth of weeds in rice fields was prepared in accordance with the same procedures as those conducted in Example 7 except that 10 parts by weight of sodium alginate was used in place of 10 parts by weight of soybean polysaccharides soluble in water.

Example 8
(Preparation of an agent for preventing the growth of weeds in rice fields)

Agent G for preventing the growth of weeds in rice fields was prepared in accordance with the same procedures as those conducted in Example 7 except that 10 parts by weight of sodium carboxymethyl-cellulose was used in place of 10 parts by weight of soybean polysaccharides soluble in water.

Example 9
(Effect of preventing the growth of weeds in rice fields)

On Jun. 12, 1998, 18 pots of 1/5000 a were filled with soil for rice fields, fertilized with an NPK chemical fertilizer (14-16-14) in an amount of 1 kg/a with respect to the N component and prepared for transplantation. On June 13, dilute dispersions of agents C to G for preventing the growth of weeds in rice fields which had been prepared in Examples 7 to 11, respectively, each having a concentration of the active carbon of 20 ppm, were applied to the pots using a spraying can so that the depth of water covering the soil was 5 cm. Turbidity of the dispersions decreased with time and the dispersions were added repeatedly about every 10 days. Thus, the second addition was conducted on June 23 and the third addition was conducted on July 3. All tests were conducted in three runs in each condition including the pots to which no agent was added. On July 13, weeds grown in the pots to which no agent was added and in the pots to which the agent was added three times were examined and the number and the dried weight of the weeds per one pot were obtained.

In the pots to which no agent was added, the number of the weeds was 426 and the dried weight of the weeds was 15.1 g. In the pots to which the dispersion containing agent C was applied three times, the number of the weeds was 31 and the dried weight of the weeds was 1.4 g. In the pots to which the dispersion containing agent D was applied three times, the number of the weeds was 38 and the dried weight of the weeds was 1.3 g. In the pots to which the dispersion containing agent E was applied three times, the number of the weeds was 42 and the dried weight of the weeds was 1.5 g. In the pots to which the dispersion containing agent F was applied three times, the number of the weeds was 33 and the dried weight of the weeds was 1.2 g. In the pots to which the dispersion containing agent G was applied three times, the number of the weeds was 37 and the dried weight of the weeds was 1.4 g.

The obtained results are shown in Table 4.

TABLE 4

| agent | | dispersant | number of weeds (/pot) | dried weight of weeds (g/pot) |
|---|---|---|---|---|
| no application of agent | — | — | 426 | 15.1 |
| agent applied three times | C | soybean polysaccharides soluble in water | 31 | 1.4 |
|  | D | tapioca starch | 38 | 1.3 |
|  | E | caramel | 42 | 1.5 |
|  | F | sodium alginate | 33 | 1.2 |
|  | G | sodium carboxy-methylcellulose | 37 | 1.4 |

The results in Table 4 show that, when dispersions of the agents for preventing the growth of weeds in rice fields of the present invention having a concentration of the active carbon of 20 ppm were applied three times, both number and dried weight of the weeds decreased to one tenth or less of the corresponding values obtained without using the agents and that the agents of the present invention exhibit a remarkable effect of preventing the growth of weeds. It is important in growing rice that the growth of weeds be suppressed in the period of one month after the transplantation of rice plants. Thus, it was confirmed that the problem of weeds in rice fields can be solved by three repeated applications of the dispersion of the agent for preventing the growth of weeds in rice fields of the present invention having a the concentration of the active carbon of 20 ppm.

What is claimed is:

1. A herbicidal composition for preventing the growth of weeds in rice fields which comprises (a) active carbon in a powder form dispersed in water in the presence of (b) a starch or a derivative of starch.

2. A herbicidal composition according to claim 1, wherein the content of the starch or the derivative of starch is 1 to 40% by weight based on the total weight of the herbicidal composition.

3. A herbicidal composition according to claim 1, wherein the active carbon is in an amount of 1 to 40% by weight based on the total weight of the herbicidal composition.

4. A herbicidal composition according to claim 3, wherein the content of the starch or the derivative of starch is 1 to 40% by weight based on the total weight of the herbicidal composition.

5. A herbicidal composition according to claim 1, wherein the active carbon has particles with an average diameter of 20 $\mu$m or less.

6. A herbicidal composition according to claim 5, wherein the content of the starch or the derivative of starch is 1 to 40% by weight based on the total weight of the herbicidal composition.

7. A herbicidal composition according to claim 5, wherein the active carbon is in an amount of 1 to 40% by weight based on the total weight of the herbicidal composition.

8. A herbicidal composition according to claim 7, wherein the content of the starch or the derivative of starch is 1 to 40% by weight based on the total weight of the herbicidal composition.

9. A herbicidal composition according to claim 8, wherein the active carbon has particles with an average diameter of 10 $\mu$m or less.

10. A herbicidal composition according to claim 8, wherein the active carbon has particles with an average diameter of 5 $\mu$m or less.

11. A herbicidal composition according to claim 10, wherein the active carbon is in an amount of 5 to 30% by weight based on the total weight of the herbicidal composition; and the starch or the derivative of starch is in an amount of 5 to 30% by weight based on the total weight of the herbicidal composition.

12. A herbicidal composition according to claim 11, wherein said (b) is a starch and is selected from the group consisting of corn, potato, sweet potato, cassava, wheat and rice.

13. A herbicidal composition according to claim 11, wherein said (b) is a derivative of starch and is selected from the group consisting of soluble starch, dextrin, British gum and oxidized starch.

14. A method for preventing the growth of weeds in rice fields comprising applying to water in rice fields in which the growth of weeds is to be prevented, an active carbon containing herbicidal composition according to claim 1 in an amount sufficient to provide a concentration of the active carbon in water in the rice fields of at least 5 ppm.

15. A method according to claim 14, wherein the concentration of the active carbon is 5 to 200 ppm.

16. A method according to claim 14, wherein the concentration of the active carbon is 20 to 100 ppm.

17. A method according to claim 16, wherein the weeds comprise at least one weed selected from the group consisting of *Monochoria vaginalis* var. plantaginea Solms-Laub., Cyperacae, *Rotala indica* Koehne var. Uliginosa Miq., *Lindernia pyxidaria*L. and *Elatine orientalis* Maskino.

* * * * *